(12) United States Patent
Liphardt et al.

(10) Patent No.: US 8,638,437 B2
(45) Date of Patent: *Jan. 28, 2014

(54) SYSTEM AND METHOD OF ALIGNING A SAMPLE

(75) Inventors: Martin M. Liphardt, Lincoln, NE (US); Blaine D. Johs, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 244 days.

This patent is subject to a terminal disclaimer.

(21) Appl. No.: 13/373,559

(22) Filed: Nov. 18, 2011

(65) Prior Publication Data

US 2012/0092653 A1 Apr. 19, 2012

Related U.S. Application Data

(63) Continuation-in-part of application No. 12/378,400, filed on Feb. 13, 2009, now Pat. No. 8,064,055.

(60) Provisional application No. 61/065,660, filed on Feb. 14, 2008.

(51) Int. Cl.
*G01J 4/00* (2006.01)

(52) U.S. Cl.
USPC .......................................... 356/364

(58) Field of Classification Search
USPC .............................. 356/364, 369
See application file for complete search history.

(56) References Cited

U.S. PATENT DOCUMENTS

| | | | |
|---|---|---|---|
| 3,880,524 A | 4/1975 | Dill et al. ...................... 356/369 |
| 4,006,293 A | 2/1977 | Bouwhuis et al. .......... 369/44.42 |
| 4,357,696 A | 11/1982 | Bierhoff et al. ............ 369/44.13 |
| 4,503,324 A | 3/1985 | Yokota ........................ 250/201.5 |
| 4,531,162 A | 7/1985 | Tokumitsu ....................... 386/76 |
| 4,558,949 A | 12/1985 | Evans ........................... 310/239 |
| 4,589,773 A | 5/1986 | Ido et al. ........................ 356/623 |
| 4,595,829 A | 6/1986 | Neumann et al. .......... 250/201.4 |
| 4,800,447 A | 1/1989 | Toba .............................. 386/77 |
| 4,825,311 A | 4/1989 | Saito .......................... 360/77.16 |
| 4,916,555 A | 4/1990 | Hathaway et al. .............. 386/78 |
| 4,935,827 A | 6/1990 | Oldershaw et al. ......... 360/77.16 |
| 5,003,406 A | 3/1991 | Hatanaka et al. ............... 386/77 |
| 5,136,149 A | 8/1992 | Fujiwara et al. ............ 250/201.5 |
| 5,187,617 A | 2/1993 | Kaminaga ....................... 360/64 |
| 5,218,415 A | 6/1993 | Kawashima ................ 356/139.1 |
| 6,091,499 A | 7/2000 | Abraham et al. .............. 356/623 |
| 6,504,608 B2 | 1/2003 | Hallmeyer et al. ........... 356/369 |
| 6,734,967 B1 | 5/2004 | Piwonka-Corle et al. ..... 356/369 |
| 6,930,765 B2 | 8/2005 | Meeks et al. ..................... 356/73 |
| 7,084,978 B1 | 8/2006 | Liphardt ....................... 356/364 |
| 7,230,699 B1 | 6/2007 | Liphardt et al. .............. 356/364 |
| 7,304,737 B1 | 12/2007 | Liphardt et al. .............. 356/369 |
| 7,304,792 B1 | 12/2007 | Liphardt et al. .............. 359/385 |
| 8,064,055 B2 * | 11/2011 | Liphardt et al. .............. 356/364 |

OTHER PUBLICATIONS

US 2004/0179288 by Hagami et al., Pub Sep. 16, 2004.
US 2004/0117811 by Foruya et al., Pub. Jun. 17, 2004.
EP 1114979 A1 by Hoffman et al, Pub Jul. 11, 2001.
EP 950881 A2 by Abraham et al, Pub Oct. 20, 1999.

\* cited by examiner

*Primary Examiner* — Roy M Punnoose
(74) *Attorney, Agent, or Firm* — James D. Welch

(57) ABSTRACT

A system and method of use thereof that enables determining and setting sample alignment based on the location of, and geometric attributes of a monitored image formed by reflection of an electromagnetic beam from a sample and into an image monitor, which beam is directed to be incident onto the sample along a locus which is substantially normal to the surface of the sample.

14 Claims, 13 Drawing Sheets

SYSTEM AND METHOD OF ALIGNING A SAMPLE

CROSS REFERENCE TO EXISTING APPLICATIONS

This Application is a CIP of application Ser. No. 12/378,400 Filed Feb. 12, 2009, and therevia Claims Benefit of Provisional Application Ser. No. 61/065,660 Filed Feb. 14, 2008.

TECHNICAL FIELD

The present invention relates to systems and methods of aligning samples, and more particularly to a method of use of a system that enables determining sample alignment based on the location of, and geometric attributes of a monitored image formed by reflection of an electromagnetic beam from said sample, which beam is directed to be incident onto said sample along a locus which is substantially normal to said sample.

BACKGROUND

In the practice of reflectometry, ellipsometry, polarimetry and the like, it is critically important to know the precise angle (AOI), and plane (POI), of incidence at which a beam of electromagnetic radiation is caused to impinge upon said sample to allow accurate determination of values of sample characterizing parameters, such as the PSI and DELTA thereof. Further, it is noted that the (AOI) and (POI) can change with location on a sample surface as the result of said surface being uneven, thereby requiring alignment at each location of a sample surface investigated.

Examples of systems which are applicable to effecting sample alignment are disclosed in, for example, Patents to Liphardt or Liphardt et al. U.S. Pat. Nos. 7,084,978; 7,230,699; 7,304,792; 7,304,737 and 7,277,171. In general, prior art systems provide means for adjusting the orientation of a sample to cause a known, precise angle (AOI) and plane (POI) of incidence. It is noted that sample alignment systems generally utilize a sample supporting stage which is rotatable about axes in the plane of a sample surface, the position of which along a locus normal to the plane, of the sample surface, can also be adjusted.

It is also noted that CD players utilize a technique of applying a laser beam to read information therein, via a Cylindrical lens, and detect the shape of a beam reflected from the CD to determine appropriate head reading "height". Patents relevant to CD Head Height are U.S. Pat. Nos. 5,187,617 to Kaminaga; 5,003,406 to Hatananka et al; 4,935,827 to Oldershaw et al.; 4,916,555 to Hathaway et al.; 4,825,311 to Saito; 4,800,447 to Toba; and 4,531,162 to Tokumitsu. Known Published Applications are US2004/0179288 by Kagami et al. and US2004/0117811 by Furuya et al. Additional known Patents are U.S. Pat. Nos. 5,218,415; 4,595,829; 5,136,149; 6,091,499; 3,880,524; 4,558,949; 4,589,773; 6,504,608; 6,930,765; 4,357,696; 4,006,293; 6,734,967; 4,503,324; EP1114979A1; and EP950881A2.

What is not disclosed or fairly suggested in prior art is a method of sample alignment which enables aligning Z-height and tip/tilt with a single system that uses astigmatism to sense Z-height and beam position to sense tip/tilt. The prior art describes using astigmatism in sample alignment, but teaches away from the present invention by requiring the focusing of a beam of electromagnetism involved, onto the sample being aligned.

It is also noted that most known prior art systems utilize a beam oriented at an oblique angle of incidence to a sample to determine sample alignment.

In view of the prior art it should be appreciated that a system and method of its use that would allow alignment of a sample by monitoring, (eg. directly observing a video monitor output), the location of, and geometric attributes of an intercepted pattern formed by reflection of an electromagnetic beam, which is directed to be incident onto said sample along a locus which is substantially normal to said sample, while altering the orientation and/or "Z" position of said sample while directly observing the effect of adjustments, would provide utility.

DISCLOSURE OF THE INVENTION

A present invention system for application in a method of aligning a sample comprises:
a selection from the group consisting of:
　a source of a beam of electromagnetic radiation; and
　a source of a beam of electromagnetic radiation comprising an aperture.
Said aperture is therefore optional.
Said system further comprises:
　a stage which accepts a sample having a sample surface, which stage allows rotation about at least one axis parallel to the plane of said sample surface; and translation of the position of said stage along a locus substantially normal to said plane formed by said plane of said sample surface; and
　a multi-element detector or single element position sensitive detector; and
　an imaging means for presenting an image of said source or aperture and directing it into said multi-element detector or single element position sensitive detector.
Said system further comprises means for introducing astigmatism into said beam of electromagnetism positioned between said source and multi-element detector or single element position sensitive detector.
It is also noted that the imaging means can comprise a means for providing an image of the source or aperture at a location other than on the sample surface, in functional combination with a re-imaging means for accepting said image and presenting it to the multi-element detector or single element position sensitive detector.
A present invention method of aligning a sample comprises the steps of:
　a) providing a system comprising:
　a selection from the group consisting of:
　　a source of a beam of electromagnetic radiation; and
　　optionally a source of a beam of electromagnetic radiation and an aperture;
　said system further comprising:
　　a stage which accepts a sample having a sample surface, which stage allows rotation about at least one axis which is substantially parallel to the plane of said sample surface; and translation of the position of said stage along a locus substantially normal to said plane of said sample surface;
　　a multi-element detector or single element position sensitive detector; and
　an imaging means disposed and applied to create an image of the source, or aperture, on said multi-element detector or single element position sensitive detector.
Said method further comprises a step b) of defining a criteria for what constitutes sample alignment.

Said method further comprises the step of:
c) while:
monitoring the location of, and geometric attributes of an image pattern of a beam of electromagnetic resulting from reflection of a beam directed onto said sample into said multi-element detector or single element position sensitive detector, wherein said monitored pattern is formed;
adjusting said stage orientation by changing at least one selection from the group consisting of:
rotation of said stage about said at least one said rotational axis parallel to the plane of said sample surface; and
translation of said stage along said locus which is substantially normal to said plane formed by said plane of said sample surface;
until the location of, and geometric attributes of said monitored beam image pattern formed by said multi-element detector or single element position sensitive detector meet said step b predetermined criteria for what constitutes sample alignment.

The predetermined criteria for the location of, and geometric attributes of said observed beam image pattern formed by said multi-element detector or single element position sensitive detector are typically that said beam image pattern be substantially circular in shape and centered about a predetermined location in an image field provided by the camera and monitor means. And the predetermined central location of the substantially circular beam image in the field provided by said multi-element detector or single element position sensitive detector, can be identified by practicing a preliminary alignment procedure using a test sample.

In the foregoing, the terminology "monitored" can indicate visually viewing a monitor screen, or can indicate a computerized approach for comparing data.

It is noted that the imaging means is constructed to form sharp images in sagital and tangential planes, and wherein translation of said sample and stage along said locus which is substantially normal to said plane of the sample surface, (ie. rotational axes parallel to said plane of said sample surface), moves the image between the points wherein the sagital and tangential images are in focus. A desired condition is where the sample and stage are positioned, via translation of said sample and stage along said locus which is substantially normal to said plane of said sample surface, such that the observed image is substantially circular, and where rotation of said sample and stage around at least one rotational axis in the plane parallel to said sample surface, positions the center of said substantially circular image at a predetermined location in a field provided by the multi-element detector or single element position sensitive detector. It is noted that examples of multiple element detectors are well known (eg. CCD's). They simply comprise a plurality of detector elements. Less well known are single element detectors that provide different outputs depending on where a beam of electromagnetism impinges on them. A non-limiting example thereof is therefore identified as a Hamamatsu Model S5990-01 Detector.

A more detailed recitation of a present invention method of aligning a sample comprising the steps of:
a) providing a system comprising:
a source of a beam of electromagnetic radiation;
a collimating lens;
a cylindrical lens or curved mirror;
a beam splitter;
a focusing lens;
a sample, on a stage support that allows rotation about at least one axes parallel to the plane of a surface of said sample, and translation adjustment of the position of said stage along a locus substantially normal to said plane of said sample surface;
and
a camera and monitor means.

Said source of a beam of electromagnetic radiation is positioned to pass a beam of electromagnetic radiation through said collimating lens and then through a cylindrical lens or reflect from a curved mirror, and impinge on said beam splitter. The beam splitter serves to reflectively direct or transmissively pass at least a portion of said beam incident thereonto, through said focusing lens and onto said sample along a locus which can be, for instance, substantially perpendicular, or substantially parallel to the locus of the beam which impinges onto said beam splitter, and which beam splitter further serves to transmissively pass or reflectively direct electromagnetic radiation which reflects from said sample and passes back through said focusing lens, therethrough, and into a camera (eg. a CCD camera) and monitor means.

Said method further comprises a step b of defining a criteria for what constitutes sample alignment.
Said method then further comprises the step of:
c) while:
monitoring the location of, and geometric attributes of a pattern of a beam of electromagnetic resulting from reflection of a beam reflectively directed or transmissively passed onto said sample by said beam splitter, after it reflects from said sample then passes back through said focusing lens, and via said beam splitter into said camera and monitor means, wherein said monitored pattern is formed,
adjusting said stage orientation by changing at least one selection from the group consisting of:
rotation of said stage about at least one of said rotational axis parallel ton the plane of said sample;
and
translation of said stage along said locus which is substantially normal to said plane formed by said plane of said sample surface;
until the location of, and geometric attributes of said monitored pattern formed by said camera and monitor means meet said step b predetermined criteria for what constitutes sample alignment.

Preferred predetermined criteria for the location of, and geometric attributes of said pattern formed by said camera and monitor means are that the pattern be substantially circular in shape and centered about a predetermined location in a field provided by the camera and monitor means produced image. Further, the predetermined location in a field provided by the camera and monitor means produced image about which the substantially circular pattern is centered, is typically identified by practicing a preliminary alignment procedure using a test sample.

In the foregoing the combination of:
the collimating lens;
the cylindrical lens or curved mirror;
the beam splitter; and
the focusing lens;
comprise an example of an "imaging system".

The present invention is also an ellipsometer or polarimeter system comprising:
a source of a beam of electromagnetic radiation;
a polarizing means;
a sample supporting stage with means for adjusting stage orientation by changing at least one selection from the group consisting of:
rotation of said stage about at least one rotational axis in the plane parallel to said sample surface; and
translation of said stage along said locus which is substantially normal to said plane of said sample surface;

an analyzing means; and
a data detector.

Said ellipsometer or polarimeter system further comprises a sample alignment system comprising:
- a source of a beam of electromagnetic radiation;
- a collimating lens;
- a cylindrical lens or curved mirror;
- a beam splitter;
- a focusing lens;
- said sample supporting stage support that allows rotation about at least one axis parallel to the plane of said sample surface, and translation adjustment of the position of said stage along a locus substantially normal to said plane of said sample surface; and
- a camera and monitor means.

Said source of a beam of electromagnetic radiation is positioned to direct a beam of electromagnetic radiation through said collimating lens and then through a cylindrical lens or reflect from curved mirror, and impinge on said beam splitter. Said beam splitter then serves to reflectively direct or transmissively pass at least a portion of said beam incident thereonto, through said focusing lens and onto said sample along a locus which is substantially, for instance, perpendicular to, or parallel to, respectively, the locus of the beam which impinges onto said beam splitter. Said beam splitter further serves to transmissively pass or reflectively direct, respectively, electromagnetic radiation which reflects from said sample and passes back through said focusing lens, and into a camera and monitor means.

Additional disclosure of a present invention for use in a method of aligning a sample, includes a system comprising:
- a selection from the group consisting of:
- a source of a beam of electromagnetic radiation; and
- optionally a source of a beam of electromagnetic radiation comprising an aperture.

Said system further comprises:
- a stage which accepts a sample having a sample surface, which stage allows rotation about at least one axis parallel to the plane of said sample surface; and translation of the position of said stage along a locus substantially normal to said plane formed by said plane of said sample surface; and
- a multi-element detector or single element position sensitive detector; and
- an imaging means disposed and applied to direct an image of said source or aperture into said multi-element detector or single element position sensitive detector.

Said system further comprises means for introducing astigmatism into said beam of electromagnetism, positioned between said source and multi-element detector or single element position sensitive detector.

The imaging means which provides an image of the source or aperture, which image is located other than on said sample surface, and said imaging means is disposed and applied to create an image of the source or aperture, on said multi-element detector or single element position sensitive detector.

Said system can also involve said means for introducing astigmatism into said beam of electromagnetism being a selection from the group consisting of:
- a toroidal mirror;
- a cylindrical lens; and
- an off-axis spherical mirror.

An additional present invention system disclosure comprises:
- a selection from the group consisting of:
- a source of a beam of electromagnetic radiation; and
- a source of a beam of electromagnetic radiation comprising an aperture.

Said system further comprises:
- a first curved mirror;
- a stage which accepts a sample having a sample surface, which stage allows rotation about at least one axis parallel to the plane of said sample surface; and translation of the position of said stage along a locus substantially normal to said plane formed by said plane of said sample surface;
- a second curved mirror; and
- a multi-element detector or single element position sensitive detector.

Said first and second curved mirrors, in combination, serve as an imaging means and as a means for introducing astigmatism.

In use said source of a beam of electromagnetic radiation provides a beam of electromagnetic radiation that passes through said aperture if present, reflects from said first curved mirror and is directed it to reflect from a sample on said stage which accepts a sample, which reflects said electromagnetic beam from a surface of said sample toward said second curved mirror, which in turn reflects it into said multi-element detector or single element position sensitive detector.

Yet another present invention system embodiment comprises:
- a selection from the group consisting of:
- a source of a beam of electromagnetic radiation; and
- a source of a beam of electromagnetic radiation comprising an aperture.

Said system further comprises:
- a curved mirror;
- a beam splitter;
- a stage which accepts a sample having a sample surface, which stage allows rotation about at least one axis parallel to the plane of said sample surface; and translation of the position of said stage along a locus substantially normal to said plane formed by said plane of said sample surface; and
- a multi-element detector or single element position sensitive detector.

Said curved mirrors serve as an imaging means, and as a means for introducing astigmatism;

In use said source of a beam of electromagnetic radiation provides a beam of electromagnetic radiation that passes through said aperture if present, reflects from said curved mirror and is directed pass through said beam splitter, then reflect from a sample on said stage which accepts a sample, which reflects said electromagnetic beam from a surface of said sample back toward said beam splitter, which in turn reflects it into said multi-element detector or single element position sensitive detector.

Said system can further comprise a lens between said beam splitter and said multi-element detector or single element position sensitive detector, ao that the beam of electromagnetic radiation reflecting from aid beam splitter toward said multi-element detector or single element position sensitive detector is focused thereonto.

In general, it is to be understood that the "monitor" can be interpreted to involve a video screen, but can also, or in the alternative, be, for instance, a computer which bypasses the need to provide a viewable display but performs the function a researcher can perform by visually observing a viewable monitor screen. Further, the terminology "observed, can mean visual observation by a researcher or the like, or a comparison of data in a computer.

Methodology utilizing the recited present invention systems involves:

a) providing a recited present invention system;
b) defining a criteria for what constitutes sample alignment;

said method further comprising the step of:

c) while:

monitoring the location of, and geometric attributes of an image pattern of a beam of electromagnetic radiation resulting from reflection of a beam directed onto said sample (S), into said multi-element detector (MED) or single element position sensitive detector (SEPSD), wherein said monitored pattern is formed, adjusting said stage (STG) orientation by changing at least one selection from the group consisting of:

rotation of said stage (STG) about at least one said rotational axis in the plane parallel to said sample surface;

and translation of said stage (STG) along said locus which is substantially normal to said plane of said sample (S) surface;

until the location of, and geometric attributes of said monitored beam image pattern formed by said multi-element detector (MED) or single element position sensitive detector (SEPSD) meet said step b predetermined criteria for what constitutes sample alignment.

Said methodology an involve said imaging means (L1) (L2) being disposed and applied to create an image of the source (LS) or aperture (AP), on said multi-element detector (MED) or single element position sensitive detector (SEPSD), and further wherein said imaging means (L1) (L2) causes an intermediate image of said source (LS) or aperture (AP) to be located other than on said sample (S) surface.

It is also of benefit to realize that the present invention allows a "one-step" approach to alignment of a sample wherein sample "tilt" and "z" height can be simultaneously adjusted while viewing the effect thereof on a video screen. For instance, noting an observed image is elongated laterally can indicate a sample is too low, and observing its elongated vertically can indicate a sample is too high, while noting an image is not centrally located indicates the sample is tilted. The necessary adjustments are therefore easy to identify and the effects of performing adjustments can be visually monitored while they are being performed. Moving the sample up and down allows easy identification of the location at which the image becomes circular and therefore not too high or low, and tilting the sample about one or more axes in the plane thereof, (eg. the plane of its monitored surface), will allow easy identification of when the image is located at a predetermined "central" location, (eg. preferably centrally in the monitor field so as to allow monitoring adjustment in all directions).

It is also noted that the disclosed methodology can be automated, including use of look-up tables which identify an observed image pattern, and using associated information to cause sample movement.

Finally, the methodology of the present invention can involve performing at least one selection from the group consisting of:

storing at least some data provided by said data detector in machine readable media;
analyzing at least some of the data provided by said data detector and storing at least some of the results of said analysis in machine readable media;
displaying at least some data provided by said data detector by electronic and/or non-electronic means;
analyzing at least some of the data provided by said data detector and displaying at least some of the results of said analysis by electronic and/or non-electronic means;
causing at least some data provided by said data detector to produce a signal which is applied to provide a concrete and tangible result;
analyzing at least some of the data provided by said data detector and causing at least some thereof to produce a signal which is applied to provide a concrete and tangible result.

The present invention will be better understood by reference to the Detailed Description Section of this Disclosure, in combination with the Drawings.

BRIEF DESCRIPTION OF THE DRAWINGS

FIG. 1a' shows an alternative system for use in practicing the present invention sample alignment methodology.

FIG. 1c' is included to show that the stage supporting a sample can also be movable in directions which translate a sample

FIG. 6b' shows an alternative off-axis curved mirror configuration.

DETAILED DESCRIPTION

Figure 1A:
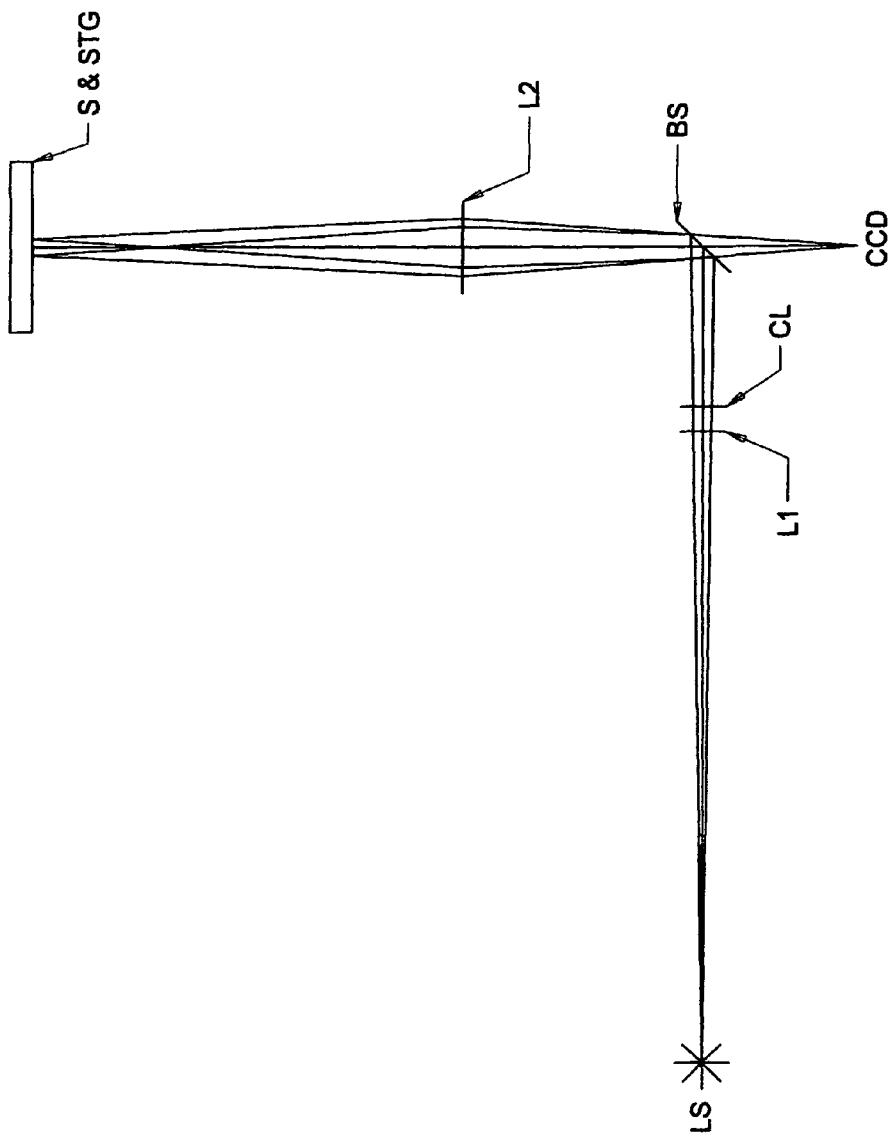
FIG. 1a shows a system for use in practicing the present invention sample alignment methodology.
Figure 1A:
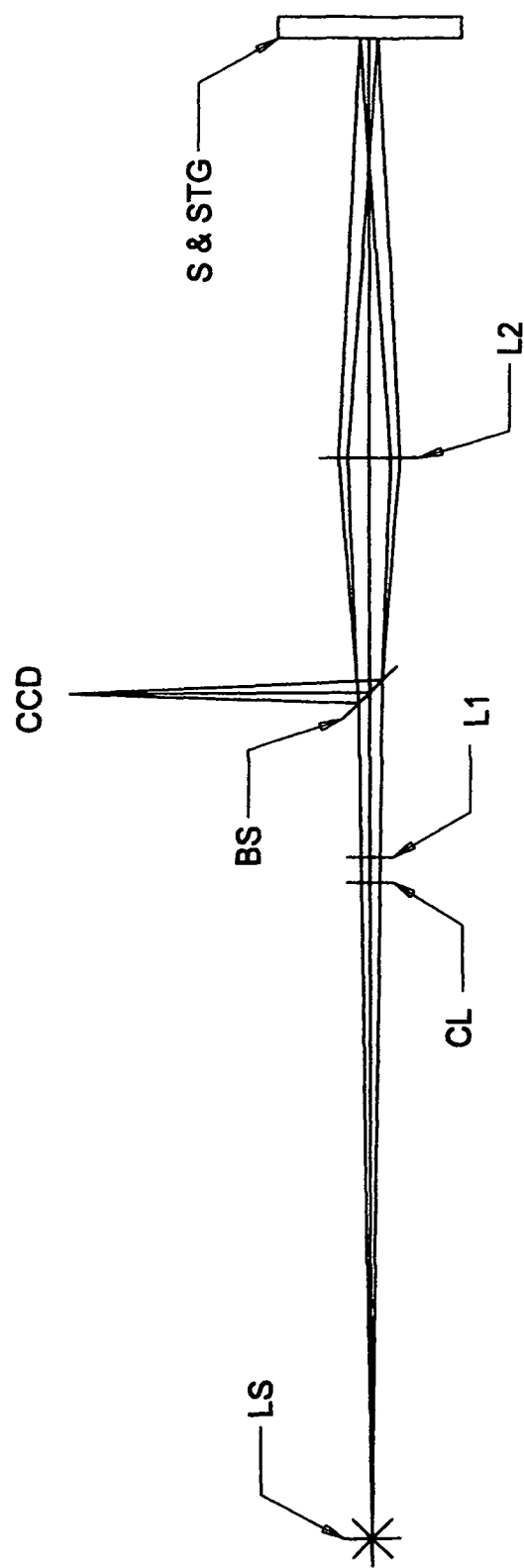
Figure 6A:
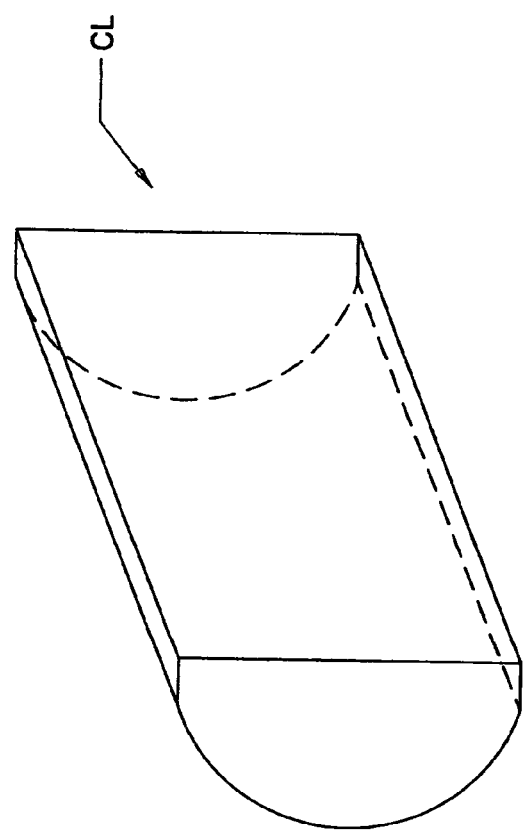
FIG. 6a shows a cylindrical lens.
Figure 6B:
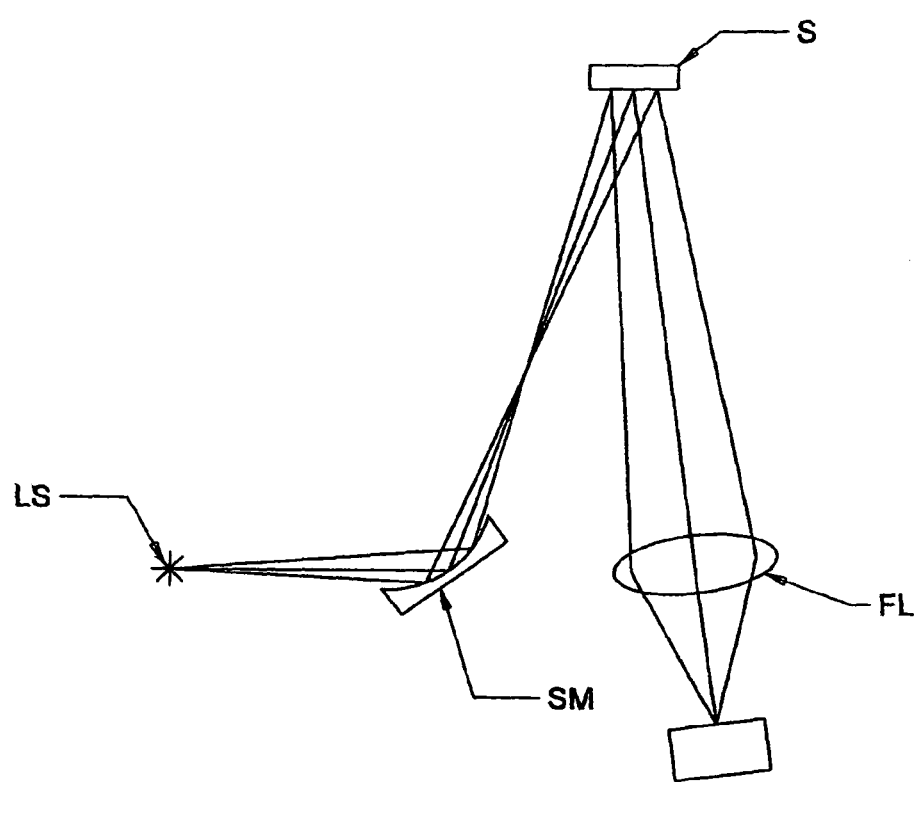
FIG. 6b shows use of an off-axis curved mirror.
Figure 6B:
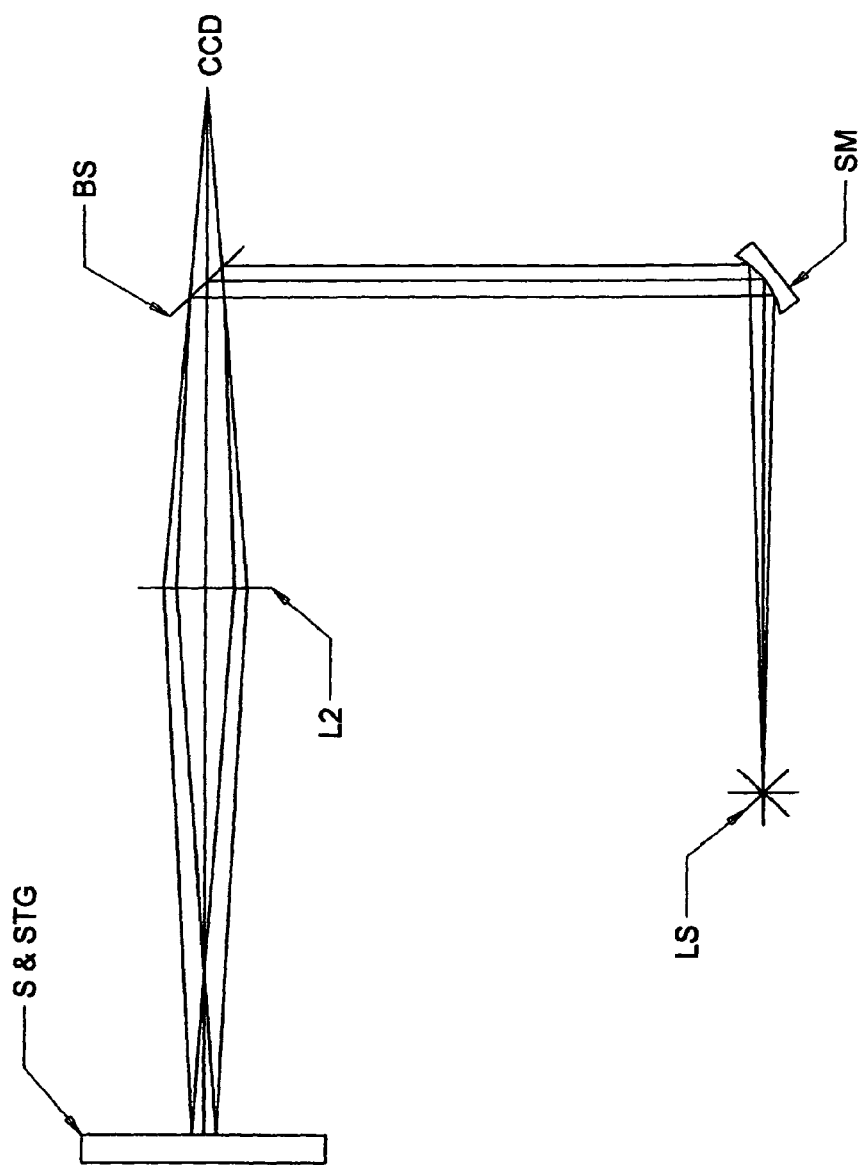

FIGS. 1a and 1a' show systems for use in practicing the present invention sample alignment methodology. Said system comprises:

a Source (LS) of a beam of electromagnetic radiation;
in either order in both FIGS. 1a and 1a':
a Collimating Lens (L1); and
a Cylindrical Lens (CL), (or Curved Mirror (SM), see FIGS. 6b and 6b');
and:
a Beam Splitter (BS);
a Focusing Lens (L2);
a Sample (S), on a Stage (STG) support that allows rotation about axes in a plane parallel to the surface of said Sample (S), and translation of the position of said stage along a locus substantially normal to said plane formed by said plane of said Sample (S) Surface; and a Camera and Monitor (CCD).

Said Source (LS) of a beam of electromagnetic radiation is positioned to direct a beam of electromagnetic radiation through said Collimating Lens (L1) and Cylindrical Lens (CL) or Curved Mirror (SM), and impinge on said Beam Splitter (BS). The Beam Splitter (BS) serves to:

reflectively direct (FIG. 1a); or transmissively pass (FIG. 1a');

at least a portion of said beam incident thereonto, through said Focusing Lens (L2) and onto said Sample (S) along a locus which is substantially, for instance, perpendicular to, or parallel to, respectively, the locus of the beam which impinges onto said Beam Splitter (BS). Said Beam Splitter (BS) further serves to transmissively pass or reflectively direct, respectively, electromagnetic radiation which reflects from said Sample (S) and passes back through said Focusing Lens (L2), into a Camera and optionally a Monitor Means, (indicated as (CCD)).

It is to be understood that in combination elements (L1) and (L2) comprise the Imaging Means, and that element (CL) serves to enter astigmatism into a beam of electromagnetic radiation interacting therewith.

Figure 1B:
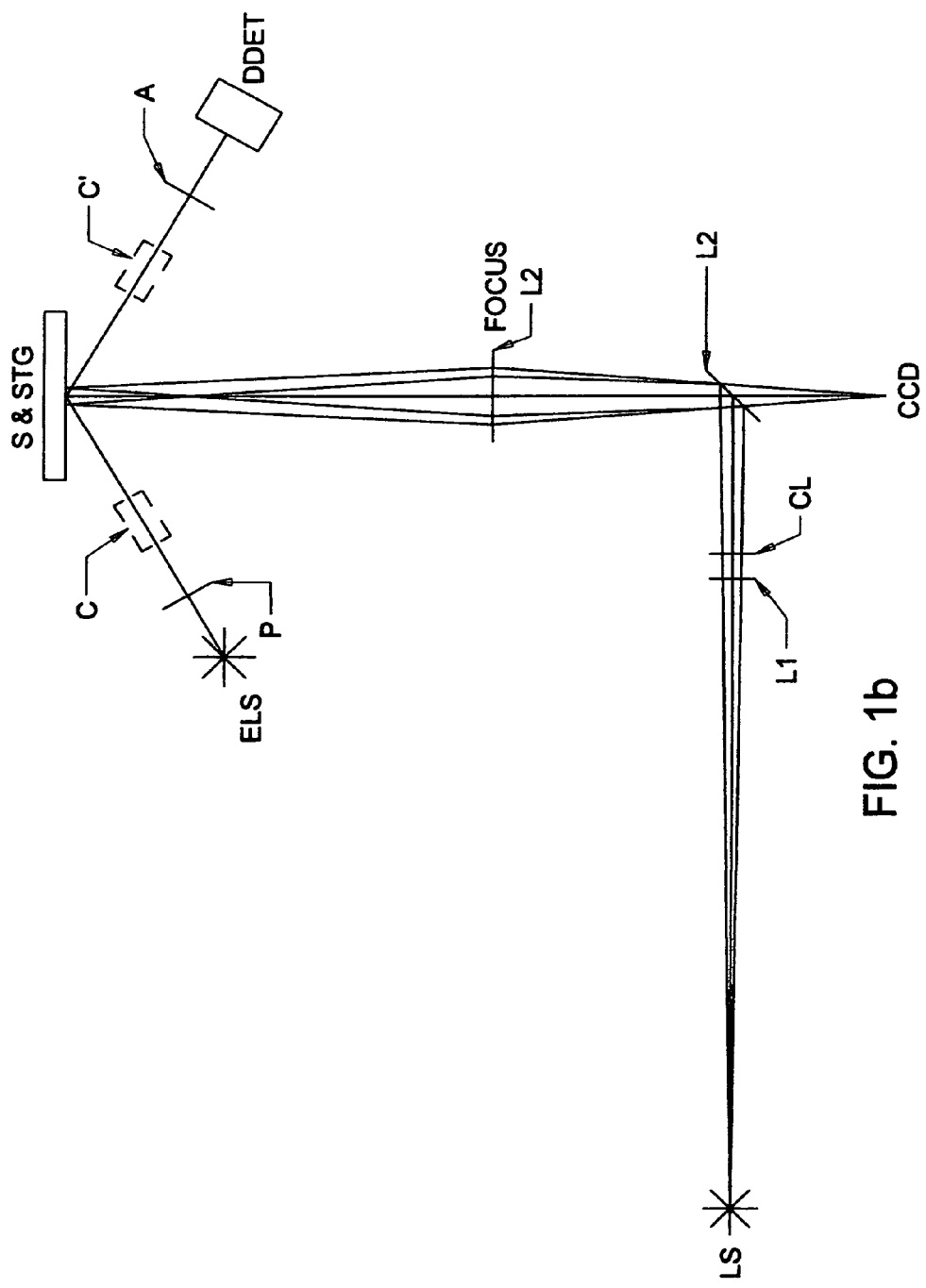
FIG. 1b shows that the present invention comprises an ellipsometer or polarimeter which includes the FIG. 1a system for use in practicing the present invention sample alignment methodology.
Figure 1C:
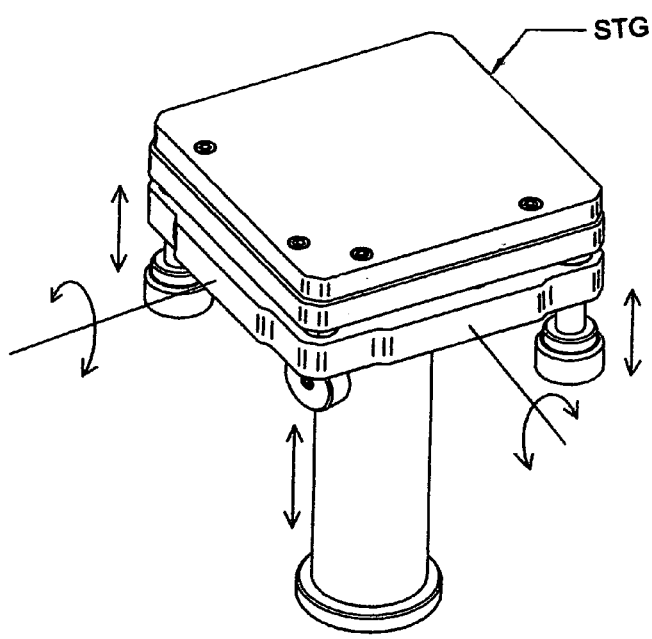
FIG. 1c is shows a stage for supporting a sample is movable in a place perpendicular to its surface, and about axes parallel to the plane of the sample surface, to effect tip/tilt.
Figure 1C:
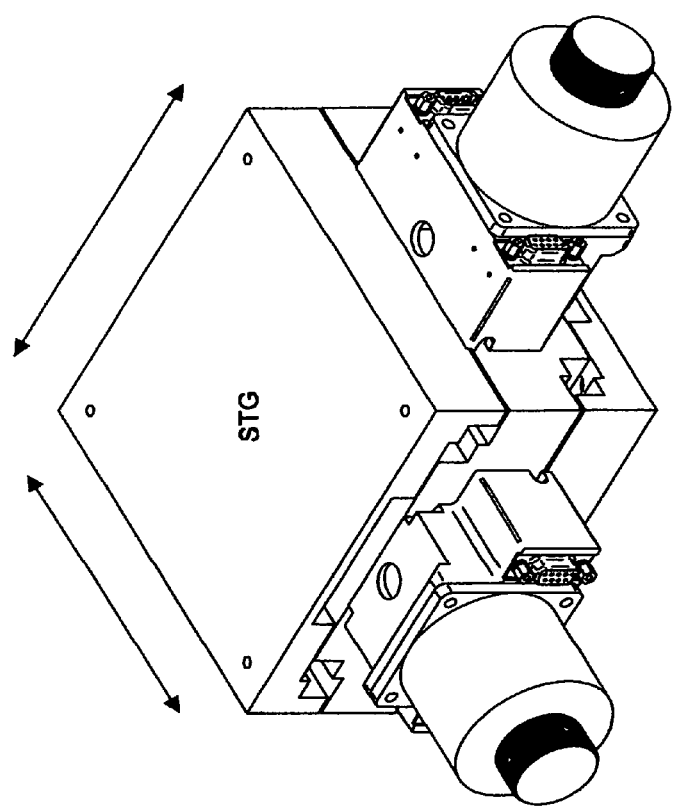

FIG. 1c shows a demonstrative Stage (STG) for supporting a Sample (S) is indicated as providing adjustment capability in a direction perpendicular to its surface, (eg. vertically), and about axes in the plane of the surface thereof to effect Tip/Tilt thereof. Note, an r-theta stage can also be used which allows radial movement as well as sample rotation to select points on a sample for investigation. FIG. 1c' is included to show that the Stage (STG) for supporting a sample can also be movable in directions which translate a sample. The motion can be motorized or effected manually.

Figure 2:
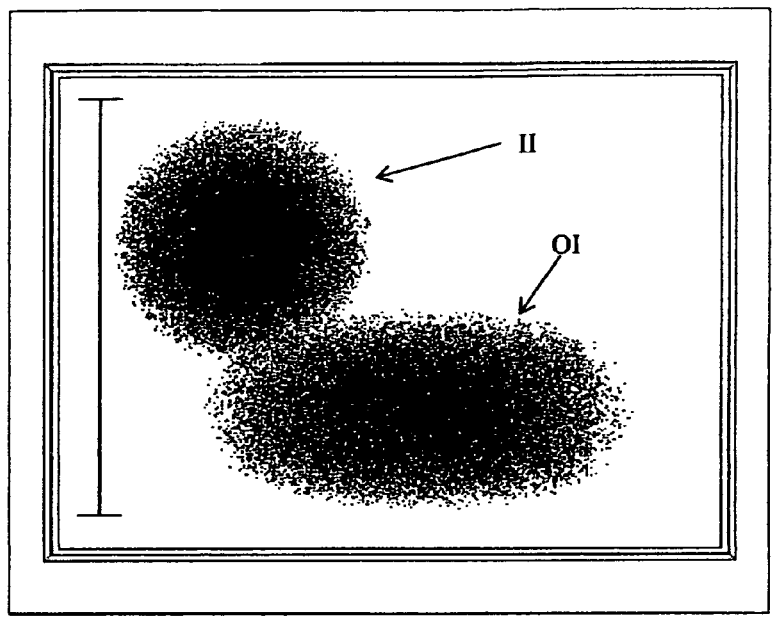
FIG. 2 shows a beam image pattern indicating that both sample tilt/tip and height orientations require adjustment.
Figure 3:
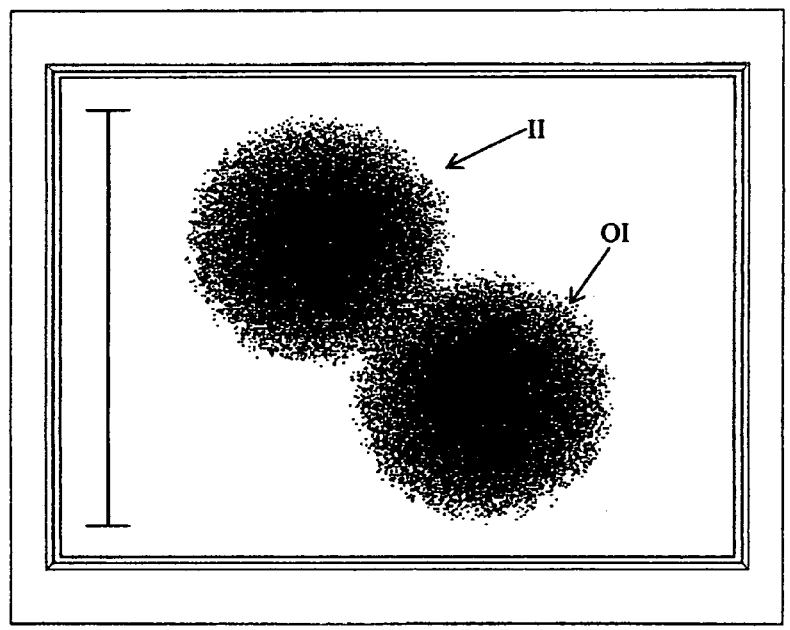
FIG. 3 shows a beam image pattern indicating that the sample, height orientation is appropriate, but that sample tilt/tip orientation requires adjustment.
Figure 4:
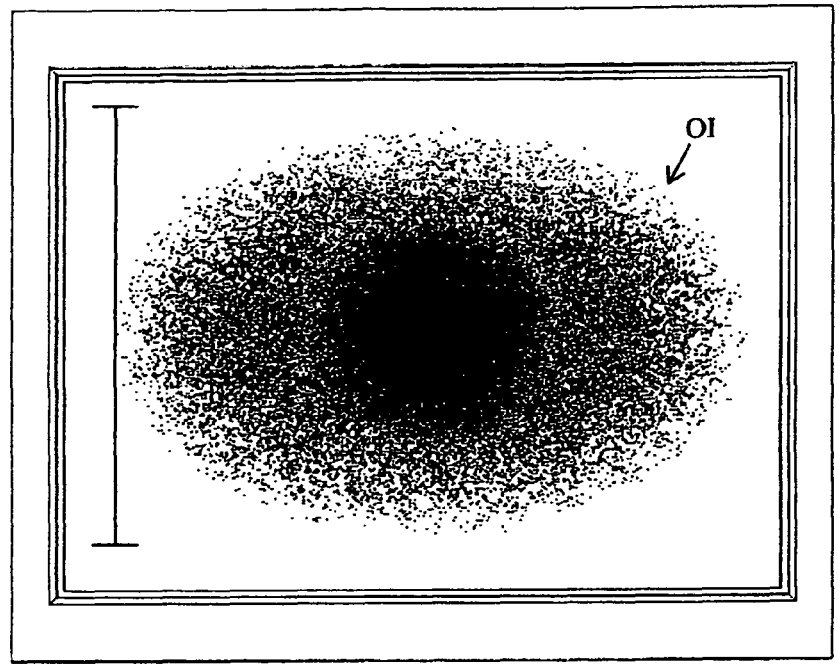
FIG. 4 shows a beam image pattern indicating that sample tilt/tip orientation is substantially correct, but that the sample height orientation requires translation in a first direction.
Figure 5:
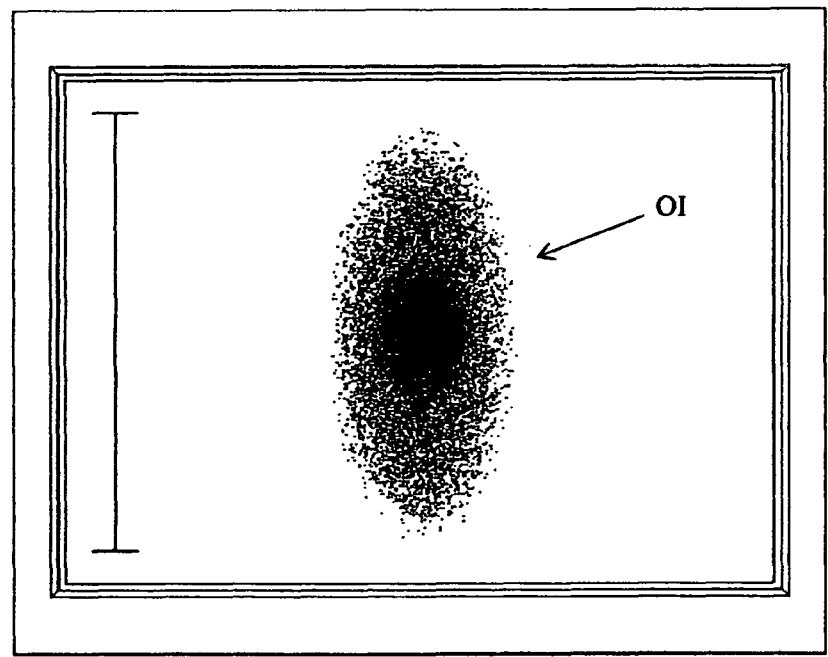
FIG. 5 shows a beam image pattern indicating that sample tilt/tip orientation is substantially correct, but that the sample height orientation requires translation in a direction opposite to that indicated in FIG. 4.

It is to be understood that the desired beam pattern produced by the Camera and Monitor Means (CCD) is circular and centered about a predetermined location in the observed Camera and Monitor Means (CCD) image field, (and/or a functional alternative). FIGS. 2-4 all show a Circular, Centrally located Intended Image (identified as (II) Computer Display FIGS. 2 and 3 as reference). FIGS. 2-4 also show Observed Images (OI). FIG. 2 shows an Observed Image (OI) pattern produced by the Camera and Monitor Means (CCD), indicating that both sample tilt/tip and height orientations require adjustment, as the Observed Image (OI) is not centered about a predetermined, (eg. central), location, and is not circular in shape as is the Intended Image (II). FIG. 3 shows an Observed Image (OI) pattern indicating that the sample height orientation is appropriate, but that sample tilt/tip orientation requires adjustment as the Observed Image (OI) is not centrally located. FIG. 4 shows an Observed Image (OI) pattern indicating that sample tilt/tip orientation is substantially correct, but that the sample height orientation requires translation in a first direction as the shape of the observed image is not circular. FIG. 5 shows an Observed Image (OI) pattern indicating that sample tilt/tip orientation is substantially correct, but that the sample height orientation requires translation in a direction opposite to that indicated in FIG. 4, as, again, the Observed Image (OI) is not circular.

In use the beam Observed Image pattern produced by the Camera and Monitor Means (CCD) is observed while the Sample Stage (STG) is rotated about at least one axis parallel to the plane of said sample surface, and/or translated along a locus which is substantially normal to the plane formed by said sample surface, until the beam image pattern appears as desired, (eg. centered at a predetermined location and circular in shape). Typically the predetermined location at which an Observe Image (OI) should be centered when the sample is properly oriented, in the center of the image field produced by the Camera and Monitor Means (CCD). Note, a central location on a Monitor is generally preferred as it allows good Sample (S) position and orientation monitoring in all rotational and translational directions.

For general information, as shown in FIG. 6a, it is also noted that a Cylindrical Lens (CL) can be described as being formed from a cylinder having a central axis, said central axis being caused to assume an arc shape. In use the electromagnetic beam is caused to impinge on the surface nearest the center of the arc the central axis is caused to assume, and pass therethrough. It is this lens shape that leads to the elongation of the beam image pattern shapes in one direction or the other, as shown in FIGS. 4 and 5, when the Sample Stage (STG) requires translation in one direction or another, to achieve proper alignment. It is noted that the use of a Cylindrical Lens (CL) or Off Axis Curved Mirror (SM) causes the imaging system to have two focal lengths, which are generally referred to as the Tangential and Sagital Planes. The present invention uses the distinct beam shape in each of said planes to sense Sample (S) Rotation about axes in the Plane of the surface of said Sample (S), and Translational position perpendicular to said Sample Surface Plane.

Turning now to FIG. 1b, it is to be understood that the present invention also comprises an ellipsometer or polarimeter system comprising:

a Source (ELS) of a beam of electromagnetic radiation;

a Polarizing means (P);

a Sample Supporting Stage (STG) with means for adjusting stage orientation by changing at least one selection from the group consisting of:

rotation of said stage about at least one rotational axis in a plane parallel to said Sample (S) surface; and translation of said stage along said locus which is substantially normal to said plane formed by said plane of said Sample (S) Surface;

an Analyzing Means (A); and a Data Detector (DDET);

said ellipsometer or polarimeter system further comprising a sample alignment system comprising:

a Source (LS) of a beam of electromagnetic radiation;

a Collimating Lens (L1);

a Cylindrical Lens (CL), (or Curved Mirror (SM), see FIG. 6b);

a Beam Splitter (BS);

a Focusing Lens (L2);

a Sample (S), on a Stage (STG) support that allows rotation about axes parallel to the plane of said Sample (S) Surface, and translation of the position of said stage along a locus substantially normal to said plane of said Sample (S) Surface; and a Camera and Monitor Means (CCD).

As described above, said Source (LS) of a beam of electromagnetic radiation is positioned to direct a beam of electromagnetic radiation through said Collimating Lens (L1) and Cylindrical Lens (CL), and impinge on said Beam Splitter (BS). The Beam Splitter (BS) serves to direct at least a portion of said beam incident thereonto, through said Focusing Lens (L2) and onto said Sample (S), along a locus which is substantially, for instance, perpendicular to the locus of the beam which impinges onto said Beam Splitter (BS). Said Beam Splitter (BS) further serves to pass electromagnetic radiation which reflects from said Sample (S) and passes back through said Focusing Lens (L2), therethrough, and into a Camera and Monitor Means (CCD), which causes an observed image on said Monitor and/or otherwise secures data.

Said ellipsometer or polarimeter can further comprise at least one Compensator (C) (C') before, and/or after the Sample (S).

As indicated above, FIG. 6a is included to show geometry of a Cylindrical Lens (CL), and FIG. 6b is included to show that an off-axis Curved, (eg. Spherical), Mirror (SM) can be used in place thereof in the present invention, and serves to demonstrate a simple system for practicing the present invention. Shown are a Source (LS) of a beam of electromagnetic radiation, a Curved Mirror (SM), a Sample (S) a Focusing Lens (FL) and a Data Detector (DDET). FIG. 6b' shows an alternative off-axis curved mirror configuration.

It is to be understood that the Camera and Monitor Means are to identified in combination by (CCD). Of course functional alternatives can also be considered as identified by (CCD). For instance, a Monitor per se. might not be present but be replaced by a means for electronically comparing data provided by the Camera. Further, the terminology "monitoring" is to be broadly interpreted to include a researcher visually observing an image on a screen as well as electronic apparatus comparing signals and the like.

Figure 7A:
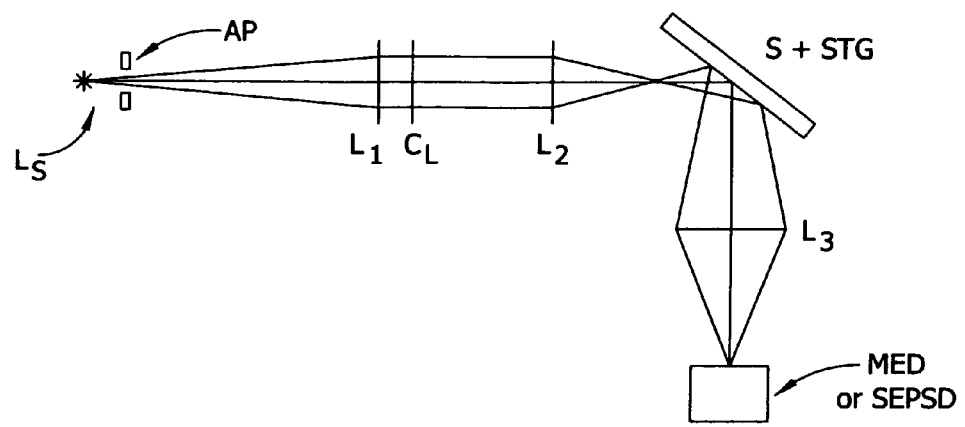
FIGS. 7a-7d show demonstrative present invention system embodiments.
Figure 7B:
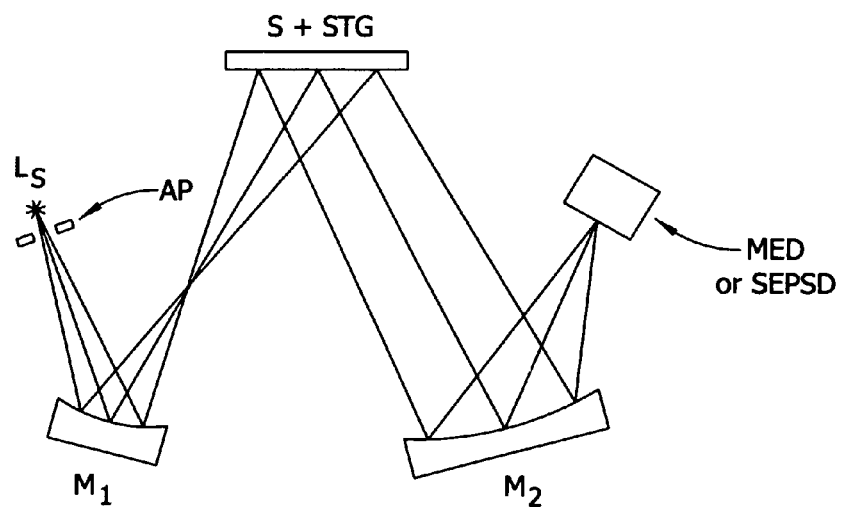
Figure 7C:
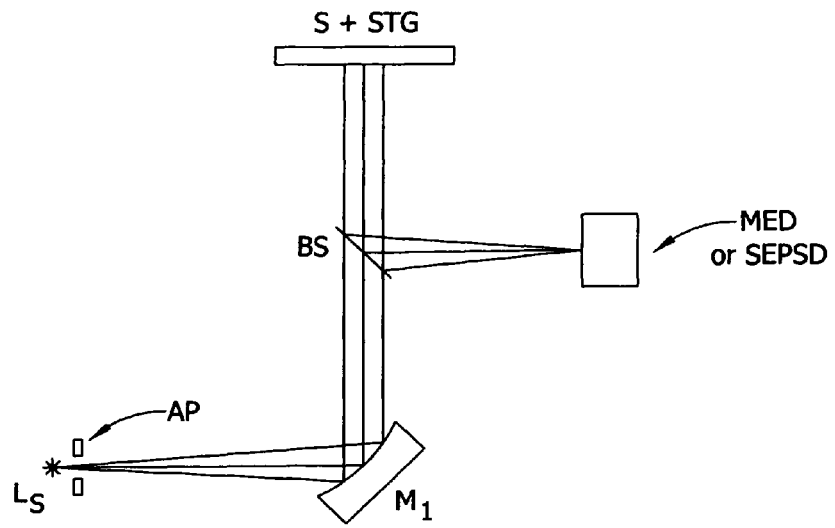

Continuing, to support disclosure, FIGS. 7a-7d are included to show specific embodiments of the present invention system. Note that FIGS. 7a and 7b do not require a Beam Splitter, while the embodiments in FIGS. 7c and 7d do include a Beam Splitter (BS). FIGS. 7b and 7c make use of Mirrors, (ie (M1) (M2)), without use of a lens. Also note that FIG. 7d makes use of both a mirror (M1) and Lens (L1). All achieve a beam of electromagnetic radiation with astigmatism introduced thereinto.

FIG. 7a shows a system for application in a method of aligning a sample comprising:
a selection from the group consisting of:
  a source (LS) of a beam of electromagnetic radiation; and
  a source (S) of a beam of electromagnetic radiation comprising an aperture (AP);
said system further comprising:
  a stage (STG) which accepts a sample having a sample (S) surface, which stage allows rotation about at least one axis parallel to the plane of said sample surface; and translation of the position of said stage along a locus substantially normal to said plane formed by said plane of said sample surface; and
  a multi-element detector (MED) or single element position sensitive detector (SEPSD); and
  an imaging means (L1) (L2) disposed and applied to direct an image of said source (LS) or aperture (AP) into said multi-element detector (MED) or single element position sensitive detector (SEPSD);
said system further comprising means for introducing astigmatism (CL) into said beam of electromagnetism, positioned between said source and multi-element detector (MED) or single element position sensitive detector (SEPSD).

Said system imaging means (L1) (L2) provides an image of the source (LS), or aperture (AP), which image is located other than on said sample surface, and said imaging means (L1) (L2) is disposed and applied to create an image of the source (LS) or aperture (AP), on said multi-element detector (MED) or single element position sensitive detector (SEPSD).

FIG. 7b shows a system for application in a method of aligning a sample comprising:
a selection from the group consisting of:
  a source (LS) of a beam of electromagnetic radiation; and
  a source (S) of a beam of electromagnetic radiation comprising an aperture (AP);
said system further comprising:
  a first curved mirror (M1);
  a stage (STG) which accepts a sample having a sample (S) surface, which stage allows rotation about at least one axis parallel to the plane of said sample surface; and translation of the position of said stage along a locus substantially normal to said plane formed by said plane of said sample surface;
  a second curved mirror (M2); and
  a multi-element detector (MED) or single element position sensitive detector (SEPSD);
said first (M1) and second (M2) curved mirrors in combination serving as an imaging imaging and as a means for introducing astigmatism;
such that in use said source (LS) of a beam of electromagnetic radiation provides a beam of electromagnetic radiation that passes through said aperture (AP) if present, reflects from said first curved mirror (M1) and is directed it to reflect from a sample (S) on said stage (STG) which accepts a sample, which reflects said electromagnetic beam from a surface of said sample (S) toward said second curved mirror (M2), which in turn reflects it into said multi-element detector (MED) or single element position sensitive detector (SEPSD).

Note that FIGS. 7a and 7b do not require a beam splitter.

Continuing, FIG. 7c shows a system for application in a method of aligning a sample comprising:
a selection from the group consisting of:
  a source (LS) of a beam of electromagnetic radiation; and
  a source (S) of a beam of electromagnetic radiation comprising an aperture (AP);
said system further comprising:
  a curved mirror (M1);
  a beam splitter (BS);
  a stage (STG) which accepts a sample having a sample (S) surface, which stage allows rotation about at least one axis parallel to the plane of said sample surface; and translation of the position of said stage along a locus substantially normal to said plane formed by said plane of said sample surface; and
  a multi-element detector (MED) or single element position sensitive detector (SEPSD);
said curved mirrors (M1) serving as an imaging imaging and as a means for introducing astigmatism;
such that in use said source (LS) of a beam of electromagnetic radiation provides a beam of electromagnetic radiation that passes through said aperture (AP) if present, reflects from said curved mirror (M1) and is directed pass through said beam splitter (BS), then reflect from a sample (S) on said stage (STG) which accepts a sample, which reflects said electromagnetic beam from a surface of said sample (S) back toward said beam splitter (BS), which in turn reflects it into said multi-element detector (MED) or single element position sensitive detector (SEPSD).

Figure 7D:
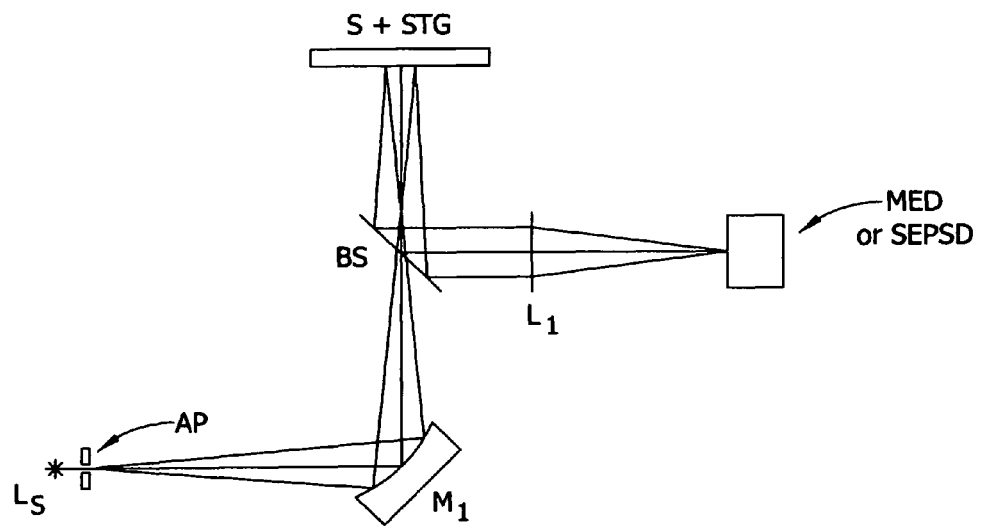

FIG. 7d shows that said system can further comprise a lens (L1) between said beam splitter (BS) and said multi-element detector (MED) or single element position sensitive detector (SEPSD), ao that the beam of electromagnetic radiation reflecting from aid beam splitter (BS) toward said multi-element detector (MED) or single element position sensitive detector (SEPSD) is focused thereonto. Note, FIG. 7d shows the optional aperture (AP) as present and the system is configured to image said aperture (AP) rather than the source (LS) as in FIGS. 7a-7c, where the optional aperture (AP) was considered not present and the source (LS) was imaged.

Figure 8A:
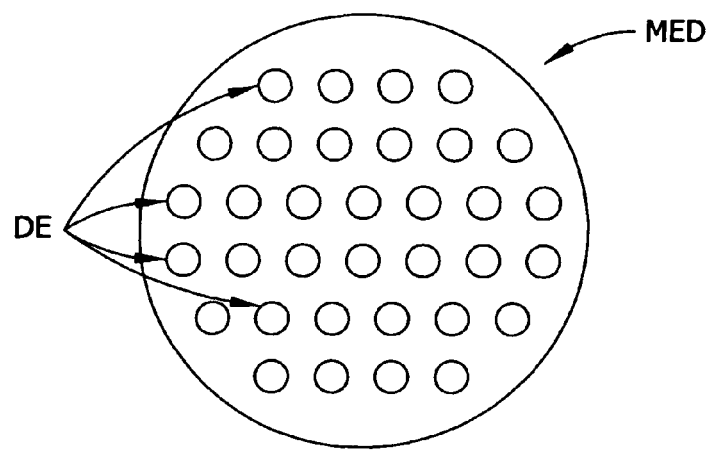
FIGS. 8a and 8b represent multi-element detector and single element position sensitive detectors, respectively.
Figure 8B:
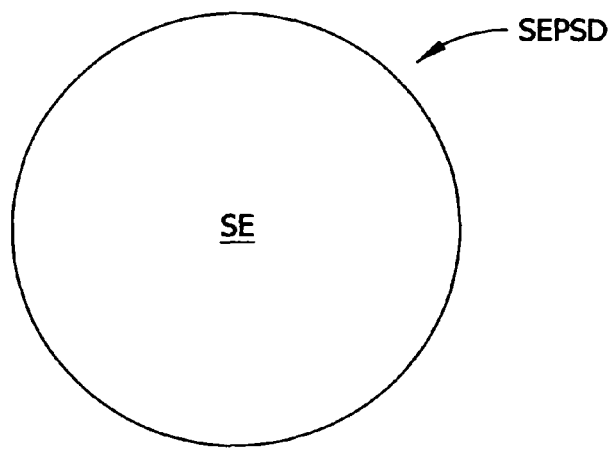

FIGS. 8a and 8b are included to represent a multi-element detector (MED) and a single element position sensitive detector (SEPSD), respectively. FIG. 8a shows many detecting elements (DE), (as in a (CCD)), and FIG. 8b a single position sensitive element (SE).

It is also noted that the terminology "astigmatism" refers to a condition entered to a beam of electromagnetism by a system characterized by focal length/power differing in orthogonally lateral directions. Further, where it is stated that an electromagnetic beam reflects from a beam splitter, it is of course meant to be realized that the beam partially reflects and is partially transmitted therethrough.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of aligning a sample comprising the steps of:
   a) providing a system comprising:
      a source (LS) of a beam of electromagnetic radiation;
      a sample (S), on a stage (STG) support that allows rotation about axes in a plane parallel to said sample surface, and translation adjustment of the position of said stage (STG) along a locus substantially normal to said plane of said sample surface;
      an imaging means (L1) (L2);
      a multi-element detector (MED) or single element position sensitive detector (SEPSD), said imaging means being disposed and applied to create an image of the source (LS) on said multi-element detector (MED) or single element position sensitive detector (SEPSD); and
      means for introducing (CL) astigmatism into said beam of electromagnetism, positioned between said source (LS) and multi-element detector (MED) or single element position sensitive detector (SEPSD);
   such that in use said source of a beam of electromagnetic radiation provides a beam of electromagnetic radiation which has astigmatism introduced thereto by said means for introducing (CL) astigmatism, and is acted on by said imaging means (L1) (L2) to create an image of the source (LS) on said multi-element detector (MED) or single element position sensitive detector (SEPSD);
   b) defining a criteria for what constitutes sample alignment;
   said method further comprising the step of:
   c) while:
      monitoring the location of, and geometric attributes of an image pattern of a beam of electromagnetic radiation resulting from reflection of a beam directed onto said sample (S), into said multi-element detector (MED) or single element position sensitive detector (SEPSD), wherein said monitored pattern is formed,
      adjusting said stage (STG) orientation by changing at least one selection from the group consisting of:
         rotation of said stage (STG) about at least one said rotational axis in the plane parallel to said sample surface;
         and
         translation of said stage (STG) along said locus which is substantially normal to said plane of said sample (S) surface;
   until the location of, and geometric attributes of said monitored beam image pattern formed by said multi-element detector (MED) or single element position sensitive detector (SEPSD) meet said step b predetermined criteria for what constitutes sample alignment.

2. A method as in claim 1 wherein the predetermined criteria for the location of, and geometric attributes of said observed beam image pattern formed by said multi-element detector (MEP) or single element position sensitive detector (SEPSD) are that said beam image pattern be substantially circular in shape and centered about a predetermined location in an image field provided by the multi-element detector (MEP) or single element position sensitive detector (SEPSD).

3. A method as in claim 2 in which the predetermined central location of the substantially circular beam image in the field provided by said multi-element detector, is identified by practicing a preliminary alignment procedure using a test sample.

4. A method as in claim 1, in which the terminology "monitored" indicates visually viewing a monitor screen which receives input from the multi-element detector (MEP) or single element position sensitive detector (SEPSD).

5. A method as in claim 1, in which the terminology "monitored" indicates a computer comparing data from the multi-element detector (MED) or single element position sensitive detector (SEPSD).

6. A method as in claim 1 wherein the imaging means is constructed to form sharp images in sagital and tangential planes, and wherein translation of said sample (S) and stage (STG) along said locus which is substantially normal to said plane formed by said rotational axis in the plane parallel to said sample surface moves the image between the points wherein the sagital and tangential images are in focus, a desired condition being where the sample and stage (STG) are positioned, via translation of said sample (S) and stage along said locus which is substantially normal to said plane of said sample (S) surface such that the observed image is substantially circular, and where rotation of said sample and stage (STG) around at least one said rotational axis in the plane parallel to the sample (S) surface positions the center of said substantially circular image at a predetermined location in a field provided by the multi-element detector (MED) or single element position sensitive detector (SEPSD).

7. A method of aligning a sample comprising the steps of:
   a) providing a system comprising:
      a source selected from the group consisting of:
         a source (LS) of a beam of electromagnetic radiation; and
         a source (LS) of a beam of electromagnetic radiation and an aperture (AP);
      said system further comprising:
         a stage (STG) which accepts a sample having a sample surface, which stage allows rotation about at least one axis which is substantially parallel to the plane of said sample surface; and translation of the position of said stage along a locus substantially normal to said plane of said sample (S) surface;
         a multi-element detector (MED) or single element position sensitive detector (SEPSD);
         an imaging means (L1) (L2) means being disposed and applied to create an image of the source (LS), or aperture (AP), on said multi-element detector (MED) or single element position sensitive detector (SEPSD); and
         means for introducing astigmatism (CL) into said beam of electromagnetism, positioned between said source (LS) and multi-element detector (MED) or single element position sensitive detector (SEPSD);

such that in use said source (LS) of a beam of electromagnetic radiation provides a beam of electromagnetic radiation which has astigmatism introduced thereto by said means for introducing astigmatism (CL), and is acted on by said imaging means (L1) (L2) to create an image of the source or aperture on said multi-element detector (MED) or single element position sensitive detector (SEPSD);
  b) defining a criteria for what constitutes sample alignment;
said method further comprising the step of:
  c) while:
    monitoring the location of, and geometric attributes of an image pattern of a beam of electromagnetic resulting from reflection of a beam directed onto said sample into said multi-element detector or single element position sensitive detector, wherein said monitored pattern is formed;
    adjusting said stage orientation by changing at least one selection from the group consisting of:
      rotation of said stage about said at least one said rotational axis parallel to the plane of said sample surface;
      and
      translation of said stage along said locus which is substantially normal to said plane formed by said plane of said sample surface;
until the location of, and geometric attributes of said monitored beam image pattern formed by said multi-element detector (MED) or single element position sensitive detector (SEPSD) meet said step b predetermined criteria for what constitutes sample alignment.

8. A method as in claim 7 wherein said imaging means (L1) (L2) is disposed and applied to create an image of the source (LS) or aperture (AP), on said multi-element detector (MED) or single element position sensitive detector (SEPSD), and further wherein said imaging means (L1) (L2) causes an intermediate image of said source (LS) or aperture (AP) to be located other than on said sample (S) surface.

9. A system for application in a method of aligning a sample comprising:
  a selection from the group consisting of:
    a source (LS) of a beam of electromagnetic radiation; and
    a source (S) of a beam of electromagnetic radiation comprising an aperture (AP);
  said system further comprising:
    a stage (STG) which accepts a sample having a sample (S) surface, which stage allows rotation about at least one axis parallel to the plane of said sample surface; and translation of the position of said stage along a locus substantially normal to said plane formed by said plane of said sample surface; and
    a multi-element detector (MED) or single element position sensitive detector (SEPSD); and
    an imaging means (L1) (L2) disposed and applied to direct an image of said source (LS) or aperture (AP) into said multi-element detector (MED) or single element position sensitive detector (SEPSD);
said system further comprising means for introducing astigmatism (CL) into said beam of electromagnetism, positioned between said source and multi-element detector (MED) or single element position sensitive detector (SEPSD).

10. A system as in claim 9 in which said imaging means (L1) (L2) is disposed and applied to create an image of the source (LS) or aperture (AP), on said multi-element detector (MED) or single element position sensitive detector (SEPSD), and said imaging means (L1) (L2) which provides an image of the source (LS), or aperture (AP), which image is located other than on said sample surface.

11. A system as in claim 9 in which said means for introducing astigmatism into said beam of electromagnetism is a selection from the group consisting of:
  a toroidal mirror;
  a cylindrical lens; and
  an off-axis spherical mirror.

12. A method of aligning a sample comprising the steps of:
  a) providing a system for application in a method of aligning a sample comprising:
    a selection from the group consisting of:
      a source (LS) of a beam of electromagnetic radiation; and
      a source (S) of a beam of electromagnetic radiation comprising an aperture (AP);
    said system further comprising:
      a first curved mirror (M1);
      a stage (STG) which accepts a sample having a sample (S) surface, which stage allows rotation about at least one axis parallel to the plane of said sample surface; and translation of the position of said stage along a locus substantially normal to said plane formed by said plane of said sample surface;
      a second curved mirror (M2); and
      a multi-element detector (MED) or single element position sensitive detector (SEPSD);
    said first (M1) and second (M2) curved mirrors in combination serving as an imaging means, and as a means for introducing astigmatism;
    such that in use said source (LS) of a beam of electromagnetic radiation provides a beam of electromagnetic radiation that passes through said aperture (AP) if present, reflects from said first curved mirror (M1) and is directed to reflect from a sample (S) on said stage (STG) which accepts a sample, which reflects said electromagnetic beam from a surface of said sample (S) toward said second curved mirror (M2), which in turn reflects it into said multi-element detector (MED) or single element position sensitive detector (SEPSD);
  b) defining a criteria for what constitutes sample alignment;
said method further comprising the step of:
  c) while:
    monitoring the location of, and geometric attributes of an image pattern of a beam of electromagnetic resulting from reflection of a beam directed onto said sample into said multi-element detector or single element position sensitive detector, wherein said monitored pattern is formed;
    adjusting said stage orientation by changing at least one selection from the group consisting of:
      rotation of said stage about said at least one said rotational axis parallel to the plane of said sample surface;
      and
      translation of said stage along said locus which is substantially normal to said plane formed by said plane of said sample surface;
until the location of, and geometric attributes of said monitored beam image pattern formed by said multi-element detector (MED) or single element position sensitive detector (SEPSD) meet said step b predetermined criteria for what constitutes sample alignment.

13. A method of aligning a sample comprising the steps of:
  a) providing a system for application in a method of aligning a sample comprising:
    a selection from the group consisting of:
      a source (LS) of a beam of electromagnetic radiation; and
      a source (S) of a beam of electromagnetic radiation comprising an aperture (AP);
    said system further comprising:
      a curved mirror (M1);

a beam splitter (BS);
a stage (STG) which accepts a sample having a sample (S) surface, which stage allows rotation about at least one axis parallel to the plane of said sample surface; and translation of the position of said stage along a locus substantially normal to said plane formed by said plane of said sample surface; and
a multi-element detector (MED) or single element position sensitive detector (SEPSD);
said curved mirrors (M1) serving as an imaging means and as a means for introducing astigmatism;
such that in use said source (LS) of a beam of electromagnetic radiation provides a beam of electromagnetic radiation that passes through said aperture (AP) if present, reflects from said curved mirror (M1) and is directed to partially pass through said beam splitter (BS), then reflect from a sample (S) on said stage (STG) which accepts a sample, which reflects said electromagnetic beam from a surface of said sample (S) back toward said beam splitter (BS), which in turn partially reflects it into said multi-element detector (MED) or single element position sensitive detector (SEPSD);
  b) defining a criteria for what constitutes sample alignment;
said method further comprising the step of:
  c) while:
    monitoring the location of, and geometric attributes of an image pattern of a beam of electromagnetic resulting from reflection of a beam directed onto said sample into said multi-element detector or single element position sensitive detector, wherein said monitored pattern is formed;
  adjusting said stage orientation by changing at least one selection from the group consisting of:
    rotation of said stage about said at least one said rotational axis parallel to the plane of said sample surface;
  and
    translation of said stage along said locus which is substantially normal to said plane formed by said plane of said sample surface;
until the location of, and geometric attributes of said monitored beam image pattern formed by said multi-element detector (MED) or single element position sensitive detector (SEPSD) meet said step b predetermined criteria for what constitutes sample alignment.

14. A method as in claim 13, in which said system further comprises a lens (L1) between said beam splitter (BS) and said multi-element detector (MED) or single element position sensitive detector (SEPSD), ao that the beam of electromagnetic radiation reflecting from aid beam splitter (BS) toward said multi-element detector (MED) or single element position sensitive detector (SEPSD) is focused thereonto.

* * * * *